United States Patent [19]

Sapper et al.

[11] Patent Number: 4,710,213
[45] Date of Patent: Dec. 1, 1987

[54] PROCESS FOR SEPARATING $CO_2$ FROM A GASEOUS MIXTURE

[75] Inventors: Rainer Sapper, Neuried; Helmut Kick, Irschenhausen, both of Fed. Rep. of Germany

[73] Assignee: Linde Aktiengesellschaft, Wiesbaden, Fed. Rep. of Germany

[21] Appl. No.: 841,635

[22] Filed: Mar. 20, 1986

[30] Foreign Application Priority Data

Mar. 20, 1985 [DE] Fed. Rep. of Germany ....... 3510097

[51] Int. Cl.[4] .............................................. F25J 3/02
[52] U.S. Cl. ........................................ 62/28; 62/41; 62/42
[58] Field of Search ................... 62/11, 20, 23, 24, 27, 62/32, 42, 28, 29, 30, 41

[56] References Cited

U.S. PATENT DOCUMENTS

| | | | |
|---|---|---|---|
| 3,983,711 | 10/1976 | Solomon | 62/28 |
| 4,149,864 | 4/1979 | Eakman et al. | 62/11 |
| 4,312,652 | 1/1982 | Mikulla | 62/32 X |
| 4,351,655 | 9/1982 | Styring, Jr. | 62/24 X |

FOREIGN PATENT DOCUMENTS

3515949 12/1985 Fed. Rep. of Germany .

OTHER PUBLICATIONS

"Process Improves Acid Gas Separation", Hydrocarbon Processing, May 1982, pp. 131–136.

*Primary Examiner*—Albert J. Makay
*Assistant Examiner*—Steven E. Warner
*Attorney, Agent, or Firm*—Millen & White

[57] ABSTRACT

A process for the separation of $CO_2$ from gases containing light hydrocarbons and a relatively high proportion of $CO_2$ comprises a two stage fractionation procedure. In a first fractionating stage, the entire amount of $C_1$ and $C_2$ hydrocarbons are separated from the gaseous mixture; the resultant bottoms fraction, which contains the $C_{3+}$ hydrocarbons and $CO_2$, is pumped to a higher pressure and further distilled in a second fractionating stage. During this process, the head cooling of the second fractionating stage is coupled with the bottoms heating of the first fractionating stage.

27 Claims, 1 Drawing Figure

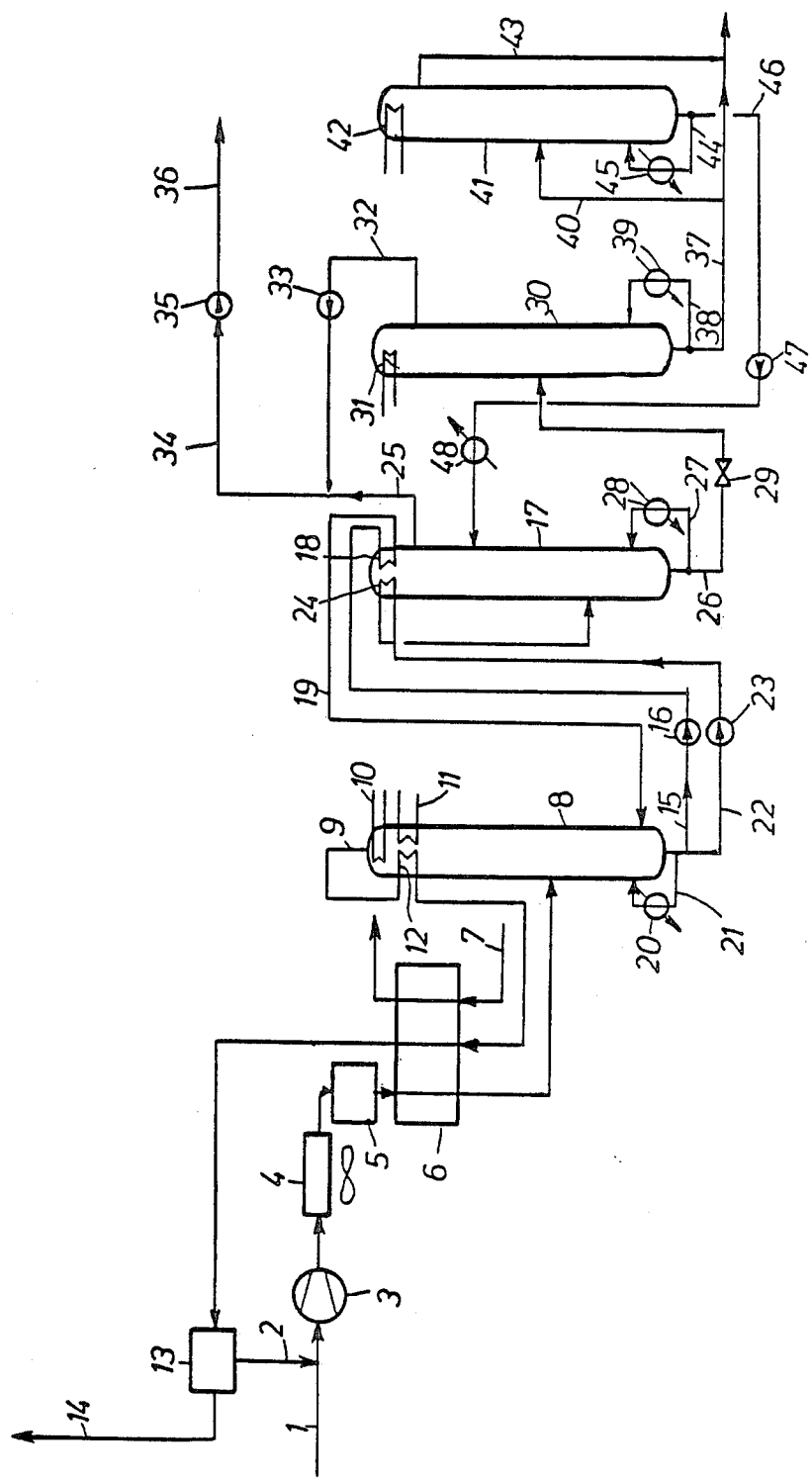

PROCESS FOR SEPARATING CO₂ FROM A GASEOUS MIXTURE

BACKGROUND OF THE INVENTION

1. Field of the Invention

The invention relates to a low temperature process for the separation of $CO_2$ from a gaseous mixture containing $CO_2$ and light hydrocarbons by a multistage distillation, wherein the gaseous mixture to be fractionated is separated, in a first fractionating stage, into an overhead fraction containing essentially all of the $C_1$ and $C_2$ hydrocarbons, as well as a portion of the $CO_2$, and into a bottoms fraction containing essentially $C_{3+}$ hydrocarbons and the largest portion of the $CO_2$; whereupon the bottoms fraction is subsequently separated into a substantially pure $CO_2$ fraction and a $C_{3+}$ hydrocarbon fraction.

2. Description Of The Prior Art

In the distillation of light hydrocarbons, especially $C_1$ to $C_6$ hydrocarbons having a relatively high proportion of $CO_2$, problems are encountered involving the freezing out of the $CO_2$. Such problems can occur, in particular, in the processing of $CO_2$-rich natural gases, i.e., natural gases having a $CO_2$ content of at least about 5%, or in tertiary petroleum extraction processes wherein $CO_2$ is injected under high pressure into deposits, i.e., underground deposits, and in addition to the recovered petroleum, an accompanying gas is obtained which contains light hydrocarbons and can include, for example, between 5 and 95% $CO_2$. This variation is caused by the $CO_2$ content gradually rising during the course of tertiary oil extraction, starting from a relatively low level to a very high level whereas the quantity of the light hydrocarbons contained in the gas remains essentially constant. While the $CO_2$ is to be mainly separated as an undesired impurity in $CO_2$-rich natural gases it is also, in the field of tertiary petroleum extraction, a desired product stream which is to be reused by reinjecting under high pressure into the deposit.

A known procedure for the separation of $CO_2$ from light hydrocarbons provides for a separation of a $C_1$ fraction from the mixture, in a first fractionating stage, followed by a fractionation of the remaining $C_{2+}$-$CO_2$ mixture into $CO_2$ and into a $C_{2+}$ fraction in a further fractionating stage. However, a number of difficulties occurs in this fractionation. While separating $CH_4$ and $CO_2$ under the conditions usually prevailing in demethanizing, solid $CO_2$ deposits form in the fractionating column. During the subsequent separation of the $CO_2$ and $C_{2+}$ hydrocarbons, $CO_2$ forms an azeotropic mixture with ethane, the azeotrope having a $CO_2$:$C_2$ ratio of about 2:1, so that effective fractionation of this mixture by distillatory methods is impossible without taking additional measures. Such additional measures include, for example, the so-called RyanHolmes process (Hydrocarbon Processing, May 1982, page 131), the introduction of additives which prevent deposition of solid $CO_2$, or are intended to break the $CO_2$-ethane azeotrope. Since these modes of operation are relatively energy intensive, a process requiring less energy has been proposed in assignee's U.S. application Ser. No. 743,727, filed June 12, 1985 (German Patent Application P No. 34 22 158.1); in this process, the first fractionating stage is not a demethanizer, but rather effects separation of essentially all the $C_1$ and $C_2$ hydrocarbons. The bottoms of this first fractionating stage yields, besides the predominant portion of $CO_2$ contained in the gaseous mixture, the $C_{3+}$ hydrocarbons which are fractionated in a single-stage or, especially in case of very high $CO_2$ contents in the gaseous mixture, a two-stage distillation, into $CO_2$ and a $C_{3+}$ hydrocarbon fraction.

OBJECTS OF THE INVENTION

Accordingly, the present invention is based on the object to provide a novel system to effect the abovedescribed separation. A preferred object is to provide an improved system of that disclosed in the aforementioned U.S. application, and particularly, to still further reduce the energy requirements of the process.

SUMMARY OF THE INVENTION

This and other objects have been attained, in a process aspect, by a process for separating $CO_2$ from a gaseous mixture containing $CO_2$ and light hydrocarbons by multistage distillation, wherein the gaseous mixture to be fractionated is separated in a first fractionating stage into an overhead fraction containing essentially all of the $C_1$ and $C_2$ hydrocarbons, as well as a portion of the $CO_2$, and into a bottoms fraction containing essentially all of the $C_{3+}$ hydrocarbons and the largest portion of the $CO_2$, and the bottoms fraction is separated, in a second fractionating stage, into a $CO_2$ fraction and into a $C_{3+}$ hydrocarbon fraction, the improvement comprising that the second fractionating stage is operated under a higher pressure than the first fractionating stage, and at least part of the bottoms heating of the first fractionating stage is effected by liquid withdrawn from the bottoms, which liquid is heated while cooling the head of the second fractionating stage and is then recycled into the bottoms of the first fractionating stage. Stated in another way, the process comprises distilling the gaseous mixture in a first column into an overhead fraction containing preferably at least 80% of the $C_1$ and $C_2$ hydrocarbons and a minor part, preferably not more than about 50% of the $CO_2$, and into a liquid bottoms fraction containing preferably at least 80% of the $C_{3+}$ hydrocarbon and the remaining $CO_2$; pumping a part of the bottoms fraction to a second column operated under a higher pressure than the first column to form a $CO_2$ overhead fraction and a $C_{3+}$ bottoms fraction; passing another part of the bottoms fraction from the first column in indirect heat exchange with the overhead of the second column to at least partially condense the $CO_2$ overhead fraction and to at least partially vaporize said another part of the bottoms fraction from the first column; and recycling resultant at least partially vaporized bottoms fraction to the bottoms of the first column to supply reboiler heat therein, said higher pressure in the second column being at least sufficient to provide a temperature of the overhead fraction therein which is higher than the temperature of the bottoms fraction from the first column.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein:

FIG. 1 is a schematic outline of a preferred embodiment of the process of gas separation.

DETAILED DISCUSSION

The thermal coupling between the bottoms of the first and the head of the second fractionating stages is believed to be an essential feature of the process of the invention. By raising the pressure level in the second fractionating stage, it is possible to elevate the column temperature and especially the head temperature to such an extent, e.g., to about 270° to 300° K., preferably 285° to 295° K., in the head, so that the required head cooling can be performed at least in part, e.g., about 10 to 100%, preferably about 30 to 100%, by indirect heat exchange with a liquid stream from the bottoms of the first fractionating stage, thereby creating a simultaneous heating and a partial vaporization of the bottoms fluid so that the recycling of the heated bottoms liquid stream into the bottoms of the first fractionating stage effects, at least in part, the necessary bottoms heating at that stage. The temperature difference between the bottoms of the first fractionating stage and the head of the second fractionating stage is about 5° to 20° K. Consequently, the need for an external supply of energy for heating the bottoms of the first fractionating stage, as well as for cooling the overhead of the second fractionating stage, is either greatly reduced or entirely eliminated; instead, it is merely necessary to pump the bottoms liquid to be fed into the second fractionating stage to the higher pressure by means of a pump, which is possible without any large energy expenditure.

The pressure difference between the two fractionating stages depends essentially on both the pressure in the first fractionating stage, usually ranging between about 20 to 50 bar, preferably between 30 and 45 bar, and also on the specific gas composition, with $CO_2$-concentrations ranging from 10 to 95%.

The pressure difference must become greater if the $C_{3+}$-concentration in the feedgas increases.

In general, the pressure difference between the two fractionating stages is between about 10 and 25 bar, preferably 13 to 20 bar.

In one embodiment of the invention, the bottoms product to be fed into the second fractionating stage, after having been pumped to the higher pressure, is heated e.g., about 5° to 15° K., while cooling the head of the second fractionating stage. This represents not only significant contribution, e.g., about 5 to 35% toward the head cooling requirements in this stage, but also a reduction in the necessary heating of the bottom of the second fractionating stage.

Care must be taken so that, in the second fractionating stage involving the further distillatory separation of the bottoms fraction of the first fractionating stage, the critical pressure of either the mixture or, respectively, of the overhead and the bottoms product, is not exceeded. The critical pressure of $CO_2$ is 73.8 bar and of propane, 42.6 bar. While conducting the process of this invention, the situation can frequently arise, particularly if the first fractionating stage is operated under a relatively high pressure, e.g., about 40 to 45 bar, that the pressure difference required or especially advantageous for thermal coupling between the bottoms of the first and the head of the second fractionating stages, i.e., about 10 to 25 bar, preferably 10 to 15 bar necessitates such a theoretical high pressure in the second fractionating stage, that the critical pressure of the $C_{3+}$ hydrocarbons is exceeded, i.e., the separation of $CO_2$-$C_{3+}$ cannot be completely achieved. In such cases, the second fractionating stage, in a further preferred embodiment of the process, is subdivided into two successive distillations wherein, in the first distillation, conducted at the higher pressure, e.g., about 50 to 65 bar, preferably 50 to 55 bar the largest portion of the $CO_2$ is discharged in essentially pure form as the overhead, whereas the bottoms produces a mixture of $C_{3+}$ hydrocarbons as well as a sufficient quantity of $CO_2$ so that the distillation is still carried out under subcritical pressure; whereupon this liquid stream obtained from the bottoms is fractionated, after expansion to a lower pressure, e.g., about 25 to 35 bar, in the second distillation so as to form essentially pure $CO_2$ as the head product and a $C_{3+}$ hydrocarbon stream as the bottoms product. Expansion of the stream takes place to a pressure level sufficiently distant from the critical pressure of the $C_{3+}$ fraction, and at which separation can be readily performed. During expansion, pressure differences of about 15–30 bar, especially about 20–25 bar, are typically bridged. The portion of $CO_2$ obtained as the overhead from the first distillation column amounts to about 70–98% of the $CO_2$ present in the first distillation column.

It is, of course, also possible to leave the amount of $CO_2$ that is obtained in the bottoms of the first distillation, representing only a relatively low proportion, e.g., about 2 to 10%, of the entire $CO_2$ present in the gaseous mixture, particularly in the case of gaseous mixtures having a high proportion of $CO_2$, for example higher than about 50% $CO_2$, in the $C_{3+}$ fraction. Consequently, the performing of the second distillation is refrained from, if the $CO_2$ proportion in the $C_{3+}$ fraction does not interfere in the utilization of this fraction and/or in cases where there is no requirement for a high recovery of $CO_2$.

In the second fractionating stage, wherein a separation takes place between the $CO_2$ and $C_{3+}$ fractions, the relative volatilities of the two fractions to be separated become relatively small at the increased pressures utilized, it may become necessary to use a large distillation column, i.e., a column having a large diameter and great height, and/or requiring a large reflux ratio in the column.

This possible problem can be readily avoided by feeding a $C_{4+}$ hydrocarbon fraction into the second fractionating stage, this fraction being supplied to the distillation column at a zone positioned above, e.g., 20 to 40 troys, the feed point of the bottoms fraction of the first fractionating stage. The addition of this fraction effectively represents an oil scrubbing stage superimposed on the distillation, which substantially simplifies the $CO_2$-$C_{3+}$ separation. This is due to the fact that the solubility of $C_3$ hydrocarbons in a $C_{4+}$ hydrocarbon fraction is much higher than the solubility of $CO_2$ therein. Therefore, the relative volatility of $CO_2$ versus $C_3$ is enhanced by addition of $C_{4+}$ hydrocarbons. A typical quantity of the $C_{4+}$ hydrocarbon fraction which is to be added to the second fractionation stage is about 8% of the gas fed to the second fractionation stage.

In this connection, it is important that the $C_{4+}$ fraction be essentially free of $C_{3-}$ and lighter hydrocarbons, since these would contaminate the $CO_2$ obtained in the column head, or would have to be separated again, causing an additional expenditure.

In another variation of this embodiment of the process, the $C_{4+}$ hydrocarbons which are returned to the second fractionating stage can be separated from the bottoms fraction which is obtained in the second fractionating stage.

Particularly when the process of this invention is conducted with the objective of obtaining a $CO_2$ product stream under very high pressures, it is advantageous to operate the second fractionating stage so that the $CO_2$ is condensed at the column head and discharged in the liquid phase, since it can then be pumped to the desired high pressure without a large expenditure of energy. This is the case, for example, in tertiary oil recovery where $CO_2$ is injected into the deposits under high pressures of up to 200 bar.

The process of this invention is suitable for the processing of $CO_2$-rich gases, i.e., gases having a $CO_2$ content of higher than 5%, particularly more than 25% $CO_2$, and is utilized with special preference in case of gases having more than about 40% or 50% $CO_2$. In some instances, the $CO_2$ content can become very high, for example, up to 95% of the gaseous mixture. The process is also suitable for the handling of gaseous mixtures having a varying $CO_2$ proportion, for example, where initially relatively low $CO_2$ proportions later rise to high $CO_2$ proportions.

The overhead of the first fractionating stage, wherein the $C_1$ and $C_2$ hydrocarbons are separated from the gaseous mixture, also contains a fraction, e.g., about 2 to 30% of the $CO_2$ from the gaseous mixture. This is because the portion of $CO_2$ corresponding to the $CO_2$ azeotrope with ethane will unavoidably be discharged overhead, together with the $C_1$-$C_2$ fraction. The particular proportion of $CO_2$ is independent of the $CO_2$ content of the feed gas mixture, and instead depends solely on the $C_2$ content of the gaseous mixture. Therefore, with a very high $CO_2$ content but a low $C_2$ content of the gaseous mixture, this loss of $CO_2$ is relatively small, wherein the amount of $CO_2$ loss becomes larger in case of gases having a relative minor $CO_2$ content and also a relatively high $C_2$ content. In order to eliminate these losses and, particularly, to be able to perform the process of this invention under favorable conditions in case of relatively low $CO_2$ contents, an additional embodiment of the invention provides that substantially the entire amount of $CO_2$ is separated from the overhead fraction of the first fractionating stage and is reintroduced into the gaseous mixture to be fractionated. Separation of the $CO_2$ from the overhead of the first fractionating stage can take place in any desired way known to those in the art, for example, by a scrubbing step or by a membrane separating method. The result of the separation is not only the obtaining of a $CO_2$-free, $C_1$-$C_2$ fraction, but also an $CO_2$ enrichment, due to the recycling of an amount of $CO_2$ corresponding to about 2.5-times the quantity of $C_2$ hydrocarbons, into the gaseous mixture; this enrichment finally leads to such high $CO_2$ concentrations, e.g., about 20 to 95%, that the $CO_2$ contained in the crude gas can be removed at the bottoms of the first fractionating stage.

It is advantageous to remove $CO_2$ at the bottom of this first separation step because this fractionation to which the whole feed gas is subjected can be operated at temperatures at which $C_3$ refrigerant can be used.

Additional details of the process according to the present invention will be described below with reference to an embodiment schematically illustrated in the figure.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following example, all temperatures are set forth uncorrected in degrees Kelvin and all parts and percentages are by mol, unless otherwise indicated.

EXAMPLE

Via conduit 1, desulfurized gas stream from a tertiary petroleum recovery process is supplied, mixed with substantially pure $CO_2$ recycled via conduit 2, and subsequently compressed in compressor 3 to a pressure of 40 bar. After cooling off the heat of compression in a cooler 4° to 312° K., the gaseous stream passes through a drying station 5 and is thereafter cooled in heat exchanger 6 to a temperature of 270° K. by indirect heat exchange with refrigerant conducted in conduit 7, and introduced into a first distillation column 8. The gaseous mixture fed into the distillation column 8 consists of 88.1% $CO_2$ and also contains 3.0% nitrogen, 5.2% methane, 0.9% ethane, 0.6% propane and 2.2% $C_{4+}$ hydrocarbons.

Column 8 operates under a pressure of 40 bar and at a bottoms temperature of 280° K. During this operation, the entire methane and ethane content are obtained in the column head, along with the nitrogen contained in the gaseous mixture, and a portion of the $CO_2$. By way of conduit 9, an overhead product is withdrawn from the column head which contains 35.9% $CO_2$, 21.3% nitrogen, 37.1% methane and 5.7% ethane. In order to maintain a head temperature of 238° K., the head of column 8 is cooled by an indirect heat exchange with the coolant streams conveyed through heat exchangers 10 and 11, as well as by means of the overhead stream which is passed through heat exchanger 12. After heating up in heat exchanger 12, the overhead is further heated in heat exchanger 6 to about 305° K. against gaseous mixture to be cooled and is subsequently conducted into a separating unit 13, for example, by a scrubber or a membrane separating unit, wherein $CO_2$ is separated from the overhead. The thus-separated $CO_2$, constituting about 4% of the amount of $CO_2$ contained in the crude feed gas, is returned via conduit 2 into the feed gaseous mixture supplied by conduit 1. The now $CO_2$-free gas from the separating unit 13 is withdrawn by way of conduit 14 and passed on, for example, to a further fractionating unit.

At 280° K., a liquid stream is obtained in the bottoms of column 8 which consists of 96.6% $CO_2$ and further includes 0.1% ethane, 0.7% propane and 2.6% $C_{4+}$ hydrocarbons. A first, partial stream of this liquid is conducted via conduit 15 and pump 16 to the head of a subsequent column 17, in order to effect head cooling at that location by indirect heat exchange in heat exchanger 18. The pump 16 is merely a conveyor pump which need not overcome large, e.g., greater than about 5 bar, pressure differences. After partial vaporization in head cooler 18, the bottoms fluid is recycled to column 8 via conduit 19 and fed into the bottoms at a temperature of 289° K. The partial stream of bottoms liquid withdrawn by way of conduit 15 accordingly effects, on the one hand, the largest portion, e.g., about 60 to 80%, of head cooling for column 17 as well as, on the other hand, the largest portion of bottoms heating for column 8. A bottoms heater 20 supplied by an external energy source is also provided in the bottoms of column 8 and is utilized for regulating purposes; if necessary, a partial stream 21 of the bottoms liquid can be passed through this heater.

The portion of the bottoms liquid obtained in column 8 which is to be further fractionated is conducted via conduit 22 to a pump 23 and pumped to a pressure of 55 bar and temperature of 282.5° K. The thereafter subcooled bottoms product is heated in heat exchanger 24 at the head of the subsequent column 17 to 289° K. and then enters the column 17.

Distillation column 17 is operated under a pressure of 55 bar and at a head temperature of 291° K. and a bottoms temperature of 353° K. In this column, the largest portion of $CO_2$ is separated, in essentially pure content, from the $C_{3+}$ hydrocarbons and withdrawn in the liquid phase from the column via conduit 25, contaminated merely by 0.1% ethane. Since the column 17 is operated above the critical pressure of the $C_{3+}$ hydrocarbons of the gaseous mixture, i.e., appr. 40 bar, it is impossible to obtain this fraction in pure form as the bottoms liquid of column 17. In order to remain an adequate distance from the critical pressure, a $CO_2$ proportion is permitted in the bottoms, so that 38.0% $CO_2$ is present in the bottoms liquid discharged via conduit 26, as well as 3.9% propane and 58.1% $C_{4+}$ hydrocarbons. A portion of this bottoms liquid stream is branched off via conduit 27, heated in heat exchanger 28 and returned into the column bottoms for the bottoms heating of column 17. The residual portion is expanded in valve 29 to a pressure of 30 bar and introduced into column 30, which operates at a head temperature of 267.5° K. and a bottoms temperature of 452° K. In this column, the residual $CO_2$, constituting less than 2% of the $CO_2$ contained in the original feed gaseous mixture, is separated from the $C_{3+}$ hydrocarbons. During this step, a heat exchanger 31 is utilized for the head cooling of column 30, a suitable refrigerant, for example, propane, being conducted through this heat exchanger. The $CO_2$ obtained in the liquid phase at the head of column 30 is withdrawn via conduit 32 and pumped by means of pump 33 to the pressure of the liquid $CO_2$ discharged from column 17 via conduit 25, i.e., 55 bar, and is subsequently combined with this liquid $CO_2$ stream. The two combined liquid $CO_2$ streams then pass via conduit 34 to a pump 35 wherein they are pumped to a desired, high final pressure, for example, about 100 to 200 bar, before exiting by way of conduit 36.

A $CO_2$-free $C_{3+}$ fraction is obtained from the bottoms of column 30 and is discharged via conduit 37. A portion, e.g., about 60 to 70%, of the bottoms liquid branches off via conduit 38, is heated in heat exchanger 39, and returned at 460° K. for heating the bottoms of column 30 into the bottoms of the latter. A portion of the $C_{3+}$ product fraction withdrawn by way of conduit 37 is conducted via conduit 40 to a further separating column 41, i.e., a distillation column wherein a separation of propane and the $C_{4+}$ hydrocarbons is performed. This column operates under a pressure of 18 bar, at a head temperature of 318° K., and at a bottoms temperature of 425° K. For head cooling, a heat exchanger 42 is utilized, which is cooled by air. A liquid propane stream is obtained as the overhead of the column and is withdrawn via conduit 43 and combined with the second partial stream discharged by way of conduit 37. The $C_{4+}$ hydrocarbons are collected in the bottoms of column 41, a partial stream of these being withdrawn via conduit 44 and being recycled, after heating to 430° K. in heat exchanger 45, for bottoms heating into the column bottoms. The remaining $C_{4+}$ product stream is withdrawn via donduit 46, pumped in pump 47 to the pressure of column 17, i.e., 55 bar, and, after cooling in heat exchanger 48, to 302° K., fed into an upper zone, e.g. 20 to 40 trays above the feed point of column 17. Even the feeding of a relatively small amount of $C_{4+}$ hydrocarbons into an upper zone of column 17 substantially facilitates the separating action in this column, which consequently enables a reduced structural height and/or reduced diameter and/or reduced reflux ratios in this column. It is, of course, not necessary to separate the $C_{4+}$ hydrocarbons to be fed into column 17 from the $C_{3+}$ fraction removed via conduit 37. Any other desired source of $C_{4+}$ components can also be utilized for this purpose. If the $C_{3+}$ fraction in conduit 17 is to be still further fractionated, e.g..into a propane fraction and a $C_{4+}$ fraction, or into a propane-butane fraction as well as a $C_{5+}$ fraction, it is, of course, also possible to conduct the entire stream through column 41 and to recycle just the partial stream of the thus-obtained heavy fraction which is required for utilization in column 17.

In the disclosed embbdiment, a $CO_2$ content of 35.9% was present in the overhead of the first fractionating stage in column 8. This amount could be further reduced in view of the fact that, based on the azeotrope formation of $CO_2$ and ethane, there is always obtained a certain residual $CO_2$ content in the overhead of column 8, for example, about 20-25%. In the present example, this has not been done since a greater amount of external refrigeration would be required for this purpose at the head of column 8; in fact, changeover from a $C_3$ refrigeration cycle to a $C_2$ refrigeration cycle would be necessary in such a case.

In a variation of the embodiment of the invention as illustrated in the figure, the head of column 41 is not cooled by air but rather by liquid withdrawn from a lower part of column 17. The liquid, after having been heated or at least partially evaporated in heat exchanger 42,is reintroduced into column 17, e.g. one tray below the tray where it was removed from, thus resulting in an intermediate heating of the lower part of column 17 and, consequently, reducing the energy demand for the sump reboiler 28. In a similar manner, a further intermediate heating of column 17 may be effected by heat exchange of further liquid withdrawn from a lower part of column 17 with crude gas or other suitable process stream, e.g. in heat exchanger 6. Furthermore, as the sump of column 38 is at a higher temperature than the sump of column 41, the liquid in line 40 may be used as heating medium in heat exchanger 45, thus also reducing the heating energy demand. In such case a further small trimmer heat exchanger may be provided for further heating of the sump of column 41, if still necessary.

Upon further study of the specification and appended claims, further objects and advantages of this invention will become apparent to those skilled in the art.

What is claimed is:

1. In a process for separating $CO_2$ from a gaseous mixture containing $CO_2$ and light hydrocarbons by multistage distillation, wherein the gaseous mixture to be fractionated is separated in a first fractionating stage into overhead fraction containing essentially all of the $C_1$ and $C_2$ hydrocarbons, as well as a portion of the $CO_2$, and into a bottoms fraction containing essentially all of the $C_{3+}$ hydrocarbons and the largest portion of the $CO_2$, and the bottoms fraction is separated, in a second fractionating stage, into a $CO_2$ fraction and into a $C_{3+}$ hydrocarbon fraction, the improvement comprising that the second fractionating stage is operated under a higher pressure than the first fractionating stage, and at least part of the bottoms heating of the first fractionating stage is effected by liquid withdrawn from the bottoms, which liquid is heated while cooling the head of the second fractionating stage and is then recycled into the bottoms of the first fractionating stage.

2. A process according to claim 1, wherein the pressure of the second fractionating stage ranges from about 10 to 25 bar higher than the pressure of the first fractionating stage.

3. A process according to claim 1, wherein the pressure of the second fractionating stage ranges about 13 to 25 bar above the pressure of the first fractionating stage.

4. A process according to claim 1, wherein the $CO_2$ separated in the second fractionating stage is withdrawn in the liquid phase and pumped to a higher pressure.

5. A process according to claim 1, wherein the temperature difference between the bottoms of the first fractionating stage and the head of the second fractionating stage ranges from about 5° to 20° K.

6. A process according to claim 1, wherein about 10 to 100% of the head cooling of the second fractionating stage is performed by the liquid stream from the bottoms of the first fractionating stage.

7. A process according to claim 1, wherein the separated $CO_2$ product is utilized in tertiary petroleum extraction processes.

8. A process according to claim 1, wherein about 30 to 100% of the head cooling of the second fractionating stage is performed by the liquid stream from the bottoms of the first fractionating stage.

9. A process according to claim 1, wherein the first fractionating stage is operated under a pressure ranging from about 20 to 50 bar.

10. A process according to claim 9, wherein the pressure of the first fractionating stage ranges from about 30 to 45 bar.

11. A process according to claim 1, wherein a $C_{4+}$ hydrocarbon fraction is fed into the second fractionating stage at a point above the feed point for the bottoms fraction of the first fractionating stage.

12. A process according to claim 11, wherein the $C_{4+}$ hydrocarbon fraction is separated from the $C_{3+}$ hydrocarbon fraction which is obtained from the bottoms present in the second distillation column of the second fractionation stage.

13. A process according to claim 1, wherein the bottom fraction from the first fractionating stage is heated by heat exchange with the head of the second fractionating stage prior to delivery of said bottom fraction to the second fractionating stage.

14. A process according to claim 13, wherein said bottom fraction is heated about 5° to 15° K. by heat exchange with the head of said second fractionating stage.

15. A process according to claim 1, wherein essentially all of the $CO_2$ which is present in the overhead fraction which is removed from the first fractionating stage is substantially separated from the remaining components present in this stage and is reintroduced into the feed gaseous mixture to be fractionated.

16. A process according to claim 15, wherein the separation of the $CO_2$ occurs in a scrubber or a membrane separating unit.

17. A process according to claim 15, wherein the $CO_2$ which is separated from the overhead fraction of the first fractionating stage and is subsequently reintroduced into the gaseous mixture to be fractionated comprises about 2 to 60 of the entire $CO_2$ content of the feed gaseous mixture.

18. A process according to claim 1, wherein the bottoms product which is passed into the second fractionating stage is first pumped to the higher pressure present in this stage and is heated while cooling the head of the second fractionating stage before being fed into the second fractionating stage.

19. A process according to claim 18, wherein the pressure of the second fractionating stage ranges about 10 to 25 bar higher than the pressure of the first fractionating stage.

20. A process according to claim 18, wherein the pressure of the first fractionating stage ranges from about 20 to 50 bar.

21. A process according to claim 20, wherein the pressure of the first fractionating stage ranges from about 30 to 45 bar.

22. A process according to claim 1, wherein the second fractionating stage comprises two successive distillations, wherein in the first distillation which is operated at the higher pressure, the largest amount of the $CO_2$ is obtained as the overhead and the bottoms product which is obtained contains $C_{3+}$ hydrocarbons and a minor amount of $CO_2$; the bottoms product is then fractionated in the second distillation, under a lower pressure than that present in the first distillation, into a $CO_2$ and a $C_{3+}$ hydrocarbon fraction.

23. A process according to claim 22, wherein the largest portion of the $CO_2$ obtained as the overhead ranges from about 70 to 98% of the $CO_2$ present in the first distillation column.

24. A process according to claim 22, wherein the pressure difference between the first and second distillation units ranges from about 15 to 30 bar.

25. A process according to claim 22, wherein the pressure in the second distillation ranges from about 20 to 25 bar below the pressure of the first distillation unit.

26. A process according to claim 22, wherein the $C_{4+}$ hydrocarbon fraction is introduced into the first distillation unit comprising the second fractionating stage at a point above the feed point for the bottoms fraction of the first fractionating stage.

27. A process according to claim 22, wherein the $CO_2$ obtained as a product from both the first and second distillation units is withdrawn from each in the liquid phase, mixed together and subsequently pumped to a higher pressure.

* * * * *